(12) United States Patent
Ariura

(10) Patent No.: US 6,468,267 B1
(45) Date of Patent: Oct. 22, 2002

(54) THERMAL THERAPY APPARATUS

(75) Inventor: Shigeki Ariura, Nakai-machi (JP)

(73) Assignee: Terumo Kabushiki Kaisha, Tokyo (JP)

( * ) Notice: Subject to any disclaimer, the term of this patent is extended or adjusted under 35 U.S.C. 154(b) by 253 days.

(21) Appl. No.: 09/635,926

(22) Filed: Aug. 10, 2000

(30) Foreign Application Priority Data

Aug. 13, 1999 (JP) .......................................... 11-229477

(51) Int. Cl.$^7$ .............................................. A61B 18/00
(52) U.S. Cl. .......................................... 606/14; 606/11
(58) Field of Search ........................ 606/11, 12, 14–15, 606/18–19

(56) References Cited

U.S. PATENT DOCUMENTS

| | | | | |
|---|---|---|---|---|
| 4,211,229 A | * | 7/1980 | Wurster ........................ | 606/14 |
| 4,672,963 A | | 6/1987 | Barken | |
| 4,932,956 A | | 6/1990 | Reddy et al. | |
| 4,932,958 A | | 6/1990 | Reddy et al. | |
| 5,049,147 A | | 9/1991 | Danon | |
| 5,207,672 A | | 5/1993 | Roth et al. | |
| 5,248,311 A | * | 9/1993 | Black et al. ................... | 606/15 |
| 5,292,320 A | | 3/1994 | Brown et al. | |
| 5,350,375 A | * | 9/1994 | Deckelbaum et al. .......... | 606/7 |
| 5,450,846 A | * | 9/1995 | Goldreyer ................... | 128/642 |
| 5,496,308 A | | 3/1996 | Brown et al. | |
| 5,769,843 A | * | 6/1998 | Abela et al. ................... | 606/10 |
| 6,171,303 B1 | * | 1/2001 | Ben-Haim et al. ............. | 606/15 |
| 6,321,109 B2 | * | 11/2001 | Ben-Haim et al. ........... | 600/424 |
| 2001/0053907 A1 | * | 12/2001 | Ota ............................. | 606/13 |

FOREIGN PATENT DOCUMENTS

| | | | |
|---|---|---|---|
| EP | 673 627 | | 9/1995 |
| JP | 6-510450 | | 11/1994 |
| JP | 2001-46389 | * | 2/2001 |
| WO | 92/04934 | | 4/1992 |
| WO | 93/04727 | | 3/1993 |

* cited by examiner

*Primary Examiner*—John A. Jeffery
(74) *Attorney, Agent, or Firm*—Burns, Doane, Swecker & Mathis, LLP

(57) ABSTRACT

A thermal therapy apparatus has a detecting device for detecting the irradiation direction of energy in thermal therapy by which energy irradiates a living body, and can thereby easily set an emission portion in a desired direction and control the thermal therapy on the basis of the detection information. This thermal therapy apparatus for performing a medical treatment by irradiating a living body with energy includes an energy generator for generating the energy, an insertion portion which can be inserted into a living body and which has a reflecting portion for performing lateral irradiation of the energy with respect to the longitudinal direction of the insertion portion, a transmitting unit for transmitting the energy generated by the energy generator to the reflecting portion, a direction detecting unit for detecting the irradiation direction of the energy in the insertion portion, and a controller for controlling the thermal therapy on the basis of information about the detection by the direction detecting unit.

14 Claims, 12 Drawing Sheets

- 125 LASER BEAM IRRADIATION DIRECTION
- 121 DISTAL PORTION
- 123 PROXIMAL PORTION
- 122 FRONT LAYER WINDOW
- BUBBLE

THERMAL THERAPY APPARATUS

FIELD OF THE INVENTION

The present invention relates to a thermal therapy apparatus for performing thermal therapy by inserting an insertion portion into a body cavity or tract such as a blood vessel, digestive tract, urinary tract, abdominal cavity, or thoracic cavity, or by surgically pushing the insertion portion against a vital tissue, and irradiating the vital tissue with energy such as a laser beam, microwave, radiofrequency, or ultrasonic wave.

BACKGROUND OF THE INVENTION

A thermal therapy apparatus is known which uses a long insertion portion to be inserted into a living body by using a body cavity or performing small incision. This insertion portion irradiates a vital tissue containing a morbid portion with energy such as a laser beam, microwave, radiofrequency, or ultrasonic wave to extinguish this morbid tissue by heating, degeneration, necrosis, coagulation, cauterization, or vaporization, thereby treating the morbid portion.

Generally, this thermal therapy apparatus irradiates a morbid portion in a surface layer or its vicinity of a vital tissue directly with energy. Another technique is also known which irradiates a deep portion of a vital tissue with energy to treat a morbid portion, such as a prostate, positioned deep in the vital tissue.

This thermal therapy apparatus treats, e.g., a prostate following a procedure described below. That is, an operator manually inserts an insertion portion into a urethra to allow an emission portion to reach a prostatic urethra (a urethra surrounded by a prostate), rotates the insertion portion in a desired energy irradiation direction around the urethra to match the direction of the emission portion with the energy irradiation direction, and irradiates the prostate with energy.

An operator generally performs the above series of operations while observing the urethra with an endoscope. Also, some thermal therapy apparatuses perform irradiation of energy not only in one direction but in a plurality of directions. In this case, an operator repeats the series of operations described above in each of these directions.

In the thermal therapy apparatus described above, an operator manually rotates the insertion portion in the energy irradiation direction around a urethra to match the direction of the emission portion with the irradiation direction. Hence, the operator cannot easily confirm the direction of the emission portion. This makes it difficult to match the direction of the emission portion with a desired energy irradiation direction, imposing a severe burden on the operator.

Also, during therapy a patient sometimes moves by reflex owing to, e.g., a feeling of physical discomfort, a feeling of burning, or a pain, and this may deviate the irradiation position or irradiation direction of an insertion portion of a medical energy irradiation apparatus. In some cases, an operator may be unaware of this deviation. As a consequence, no satisfactory effect of treating a morbid portion may be obtained, or a portion other than the target portion may be irradiated with energy.

Furthermore, when the operator notices the deviation of the position or direction of the insertion portion and wants to again match the direction of the emission portion with the desired energy irradiation direction, the direction of the emission portion may not be matched with the previously matched direction. Consequently, no satisfactory effect of treating a morbid portion may be obtained.

In a thermal therapy apparatus which performs irradiation of energy not only in one direction but also in a plurality of directions, the operation becomes cumbersome. Therefore, in irradiation of energy in one desired direction, the direction of an emission portion may be matched in a direction in which energy already irradiates.

Consequently, energy may irradiate more than needed in the same direction.

The present invention has been made in consideration of the above conventional problems, and has as its first object to provide a thermal therapy apparatus capable of readily matching the irradiation direction of energy with a desired direction by detecting the energy irradiation direction.

It is second object of the present invention to provide a thermal therapy apparatus which prevents energy irradiation to a portion other than a target portion by automatically interrupting or controlling thermal therapy even when the irradiation direction of energy deviates owing to the movement of a patient during the thermal therapy.

SUMMARY OF THE INVENTION

According to the present invention, the above object is attained by providing a thermal therapy apparatus for performing a medical treatment by irradiation of energy into a living body comprises energy generating means for generating the energy, a long insertion portion which can be inserted into the living body, an emission portion formed in the insertion portion to perform lateral irradiation of the energy with respect to a longitudinal direction of the insertion potion, direction detecting means for detecting an irradiation direction of the energy in the insertion portion, confirming means for notifying an operator of information about the detection by the direction detecting means, and control means for controlling said irradiation of the energy on the basis of the information about the detection by the direction detecting means. Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Preferred embodiments of the present invention will now be described in detail in accordance with the accompanying drawings.

Figure 1:
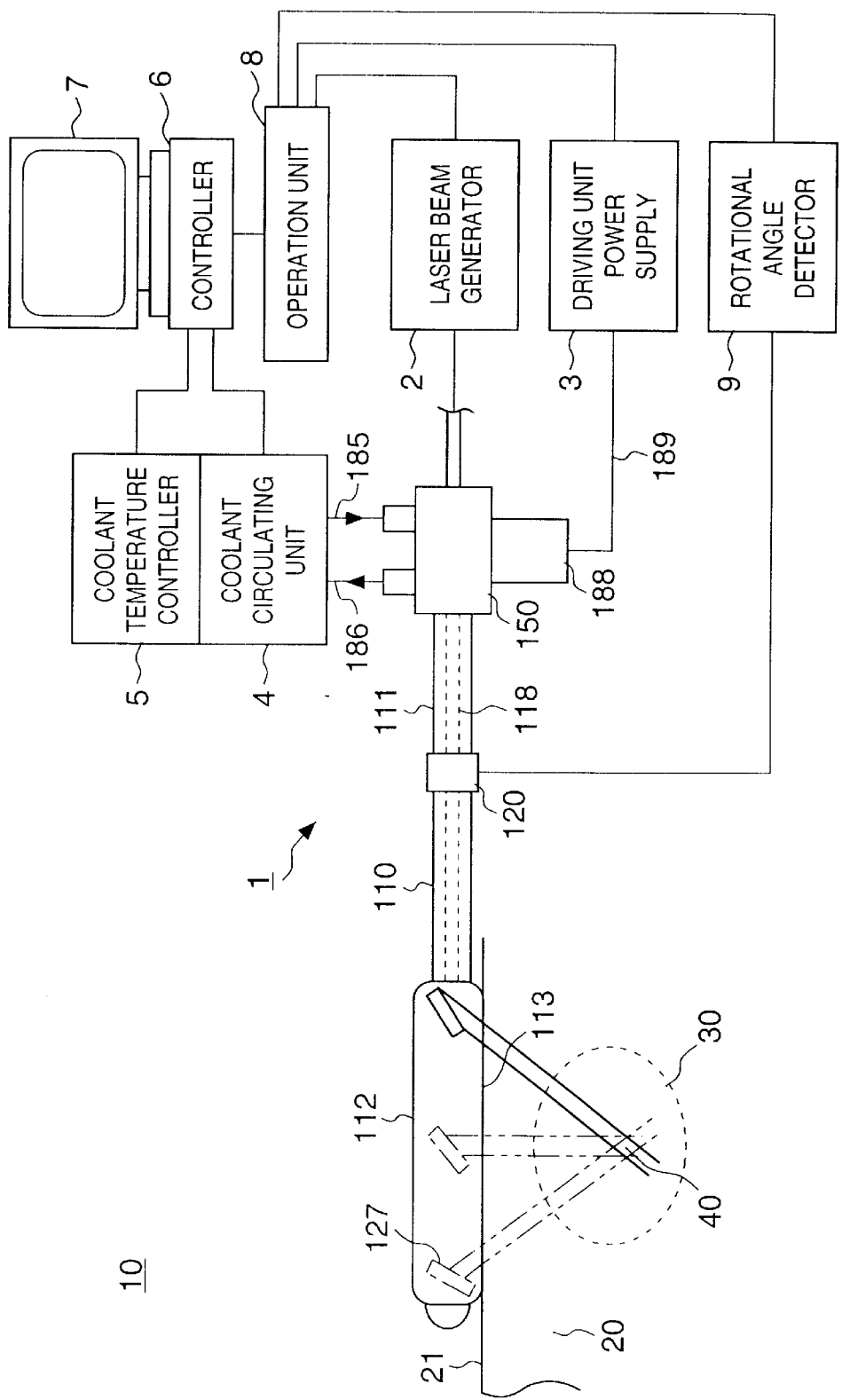
FIG. 1 is a view showing the system configuration of a thermal therapy apparatus 10 of the first embodiment.

The first embodiment will be described in detail below with reference to FIGS. 1 to 7. FIG. 1 is a view showing the system configuration of a thermal therapy apparatus 10 of the first embodiment. This thermal therapy apparatus 10 has a side-emission-type laser beam irradiation unit 1 to be inserted into a living body. A laser beam guided through an optical fiber 118 from a laser beam generator 2 irradiates a vital tissue 20 from a housing 112.

A rotational angle setting/detecting unit 120 is placed between a main body front portion 110 (to be referred to as a main body front portion hereinafter) and a main body rear portion 111 (to be referred to as a main body rear portion hereinafter) of the laser beam irradiation unit 1. This rotational angle setting/detecting unit 120 is used to determine the irradiation direction of the laser beam emitted from a laser reflecting surface 127 placed inside the housing 112 of the laser beam irradiation unit 1.

That is, the rotational angle setting/detecting unit 120 indicates the angle of a laser beam irradiation direction with respect to a reference axis (in the opposite direction to gravity) in the circumferential direction of the main body front portion 110 of the laser beam irradiation unit 1 inserted into a living body. Also, when a patient moves for some reason during thermal therapy, the rotational angle setting/detecting unit 120 detects the degree of deviation of the angle of the laser beam irradiation direction from a set value.

Furthermore, the main body front portion 110 includes a plurality of lumens (not shown) for circulating a coolant, which communicate with the housing 112 connected to the end portion of the main body front portion 110. These lumens are connected to a coolant supply tube 185 and a coolant return tube 186 of a coolant circulating unit 4.

On the basis of a control signal from a controller 6, the coolant circulating unit 4 supplies a coolant to the laser beam irradiation unit 1 at a set flow rate. On the basis of a control signal from the controller 6, a coolant temperature controller 5 controls the temperature of the coolant by heating or cooling the coolant.

A motor 188 rotates at a set rotational speed on the basis of a control signal from the controller 6. The controller 6 includes an operation unit 8 as an input means, a display unit 7 for displaying input information or system information, a control unit (not shown) for controlling each device, a storage device (not shown) for storing various pieces of information, and an input/output unit (not shown) for inputting and outputting various kinds of information.

When thermal therapy is performed, the coolant circulating unit 4 supplies a coolant to the laser beam irradiation unit 1 via the coolant supply tube 185, the motor 188 rotates, and the laser beam irradiation unit 2 operates.

A generated laser beam is guided to the distal end portion of the laser beam irradiation unit 1 by the optical fiber 118, reflected by the reflecting surface 127, transmitted through a window and a cover member 113, and irradiates a target point 40. During the operation, the reflecting surface 127 changes the irradiation angle by moving back and forth in the axial direction at a period of 0.1 to 10 Hz. Since all optical paths of the laser beam cross each other at the target point 40 in a target portion 30, the target point 40 is continuously irradiated with the laser beam and heated to a high temperature by generating a large amount of heat.

On the other hand, a surface layer 21 of the vital tissue 20 is intermittently irradiated with the laser beam and maintained at a relatively low temperature because the amount of generated heat is small. Consequently, this surface layer 21 is protected from the influence of the laser beam heating.

Figure 2:
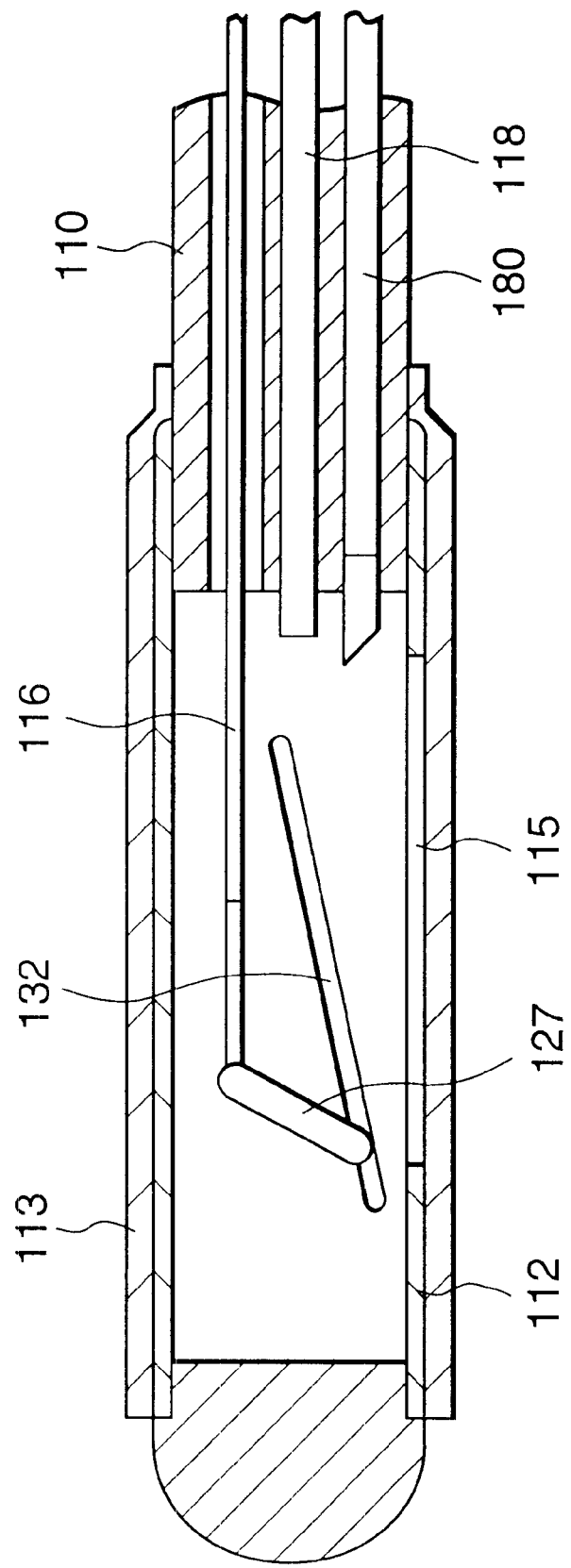
FIG. 2 is a sectional view of an end portion and its vicinity of a laser beam irradiation unit main body 110 of the first embodiment.

FIG. 2 is a sectional view of the distal end portion of the laser beam irradiation unit 1. As shown in FIG. 2, the laser beam irradiation unit 1 has the reflecting surface 127 as a smooth reflecting portion for reflecting a laser beam inside the housing 112 (the surface 127 will be referred to as a reflecting surface hereinafter).

This reflecting surface 127 is coupled with a driving unit 150 (FIG. 1) placed in the proximal end portion of the laser beam irradiation unit 1 via an arm 116. When this arm 116 is moved in the axial direction of the main body front portion 110, the reflecting surface 127 is also moved in the axial direction.

The driving unit 150 (FIG. 1) has a cam mechanism (not shown) which converts the rotation of the motor 188 (FIG. 1) into reciprocation. When the motor 188 (FIG. 1) rotates, the driving unit 150 moves the reflecting surface 127 back and forth in the axial direction of the main body front portion 110.

The housing 112 is a hard tubular glass having a laser beam irradiation window 115 and is covered with the cover member 113 having high laser beam transmittance.

Figure 3:
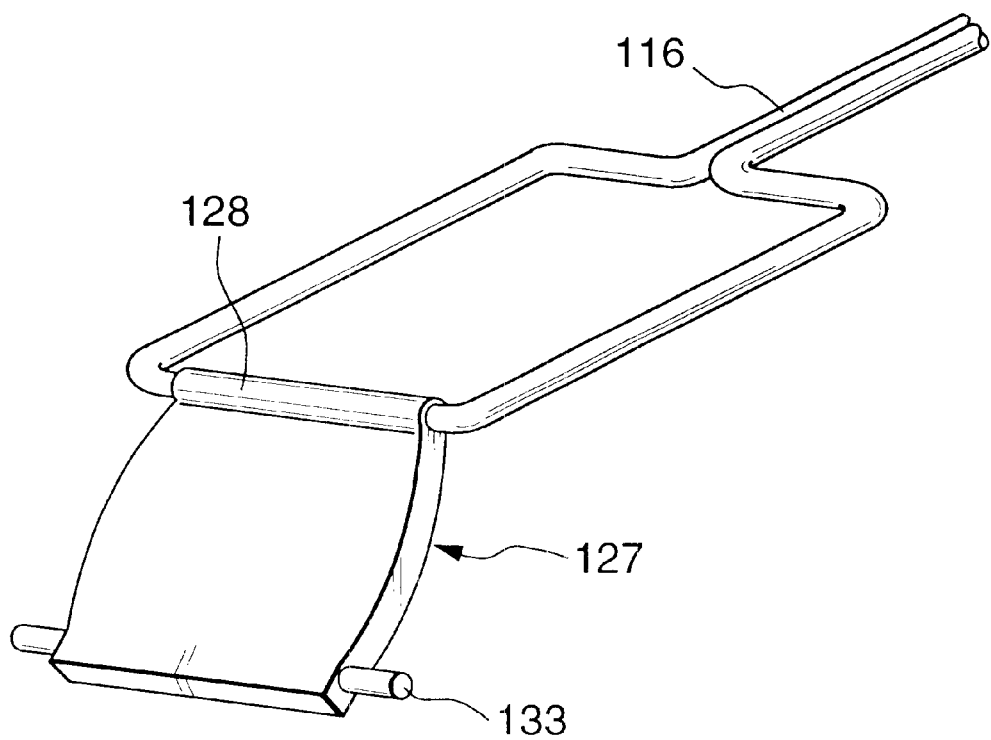
FIG. 3 is a perspective view for explaining the structures of a reflecting surface 127 and an arm 116 of a laser beam irradiation unit 1.

FIG. 3 is a perspective view for explaining the structures of the reflecting surface 127 and the arm 116 of the laser beam irradiation unit 1. The arm 116 supports the reflecting surface 127 by branching into left- and right-hand portions in the housing 112.

A support portion 128 is formed on one edge of the reflecting surface 127, and a pair of projections 133 are formed on the other edge. The support portion 128 is attached to the arm 116 so as to be freely rotatable. Therefore, the support portion 128 can rotate in accordance with changes in the angle of reflection of the reflecting surface 127.

The projections 133 fit in grooves 132 formed in inner walls of the housing 112. The arm 116 is connected to the driving unit 150 (FIG. 1) placed in the proximal end portion of the laser beam irradiation unit 1 and moves the reflecting surface 127 back and forth in the axial direction of the main body front portion 110. Accordingly, on the basis of the cooperation of the arm 116 and the grooves 132, the reflecting surface 127 changes the inclination angle in accordance with the movement in the axial direction.

Figure 4:
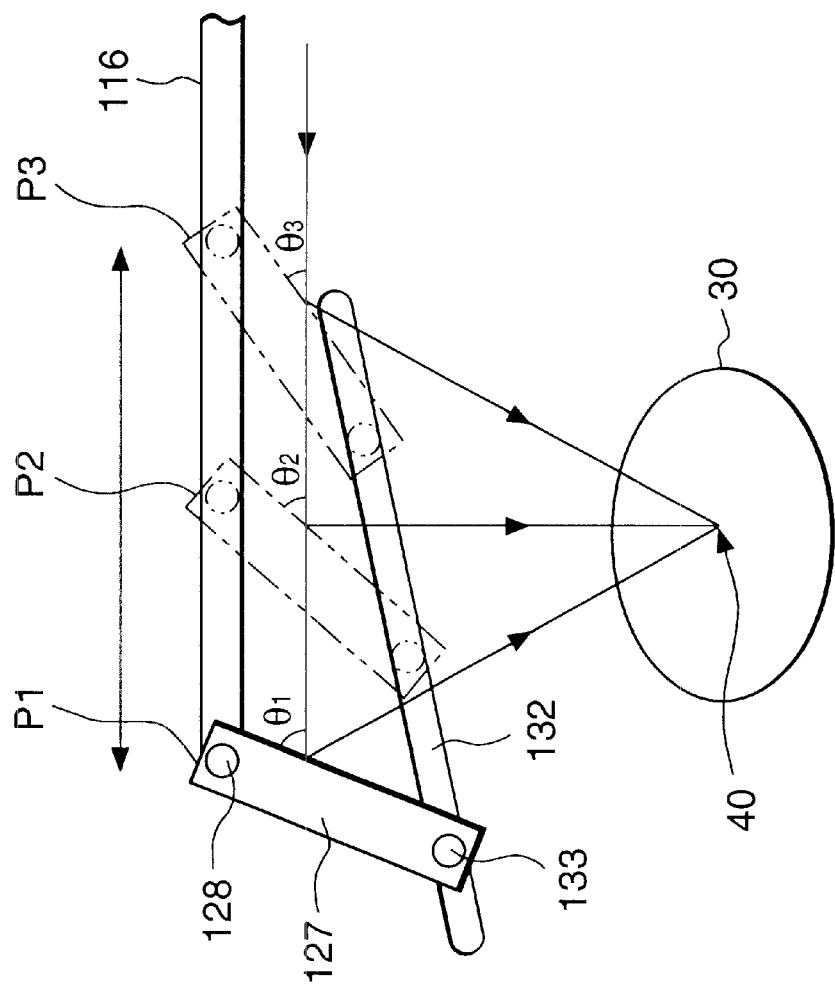
FIG. 4 is a view for explaining the relationship between the movement of the reflecting surface 127 of the laser beam irradiation unit 1 and the laser beam irradiation direction.

FIG. 4 is a view for explaining the relationship between the movement of the reflecting surface 127 and the laser irradiation direction. As shown in FIG. 4, the distance between the arm 116 and the grooves 132 not parallel to the arm 116 in a position $P_2$ is shorter than that in a position $P_1$.

Accordingly, when the support portion 128 of the reflecting surface 127 moves from the position $P_1$ to the position $P_2$ the projections 133 of the reflecting surface 127 slide along the grooves 132 to adjust the inclination angle of the reflecting surface 127.

That is, the inclination angle of the reflecting surface 127 with respect to the axis of the main body front portion 110 decreases from $\theta_1$ to $\theta_2$. Likewise, when the support portion 128 of the reflecting surface 127 moves from the position P2 to a position P3, the inclination angle of the reflecting surface 127 with respect to the axis of the main body front portion 110 further decreases from $\theta_2$ to $\theta_3$.

In these positions P1 to P3, the laser beam reflected by the reflecting surface 127 concentrates on the target point 40 in the target 30 as a portion to be heated. That is, only the target point 40 is continuously irradiated with the laser beam, and other tissues such as the surface layer are intermittently irradiated.

Accordingly, the target point 40 is heated by the laser beam to reach a desired temperature. On the other hand, other tissues such as the surface layer are hardly heated because the laser beam irradiation amount is small and hence the amount of generated heat is small.

Note that the laser beam irradiation unit 1 is applicable to morbid portions having complicated shapes by properly designing the relationship between the arm 116 parallel to the axial direction of the main body front portion 110 and the grooves 132 not parallel to the axial direction, or appropriately designing the shape of the grooves 132. For example, the grooves 132 need not be straight grooves but can be curved grooves.

Figure 5:
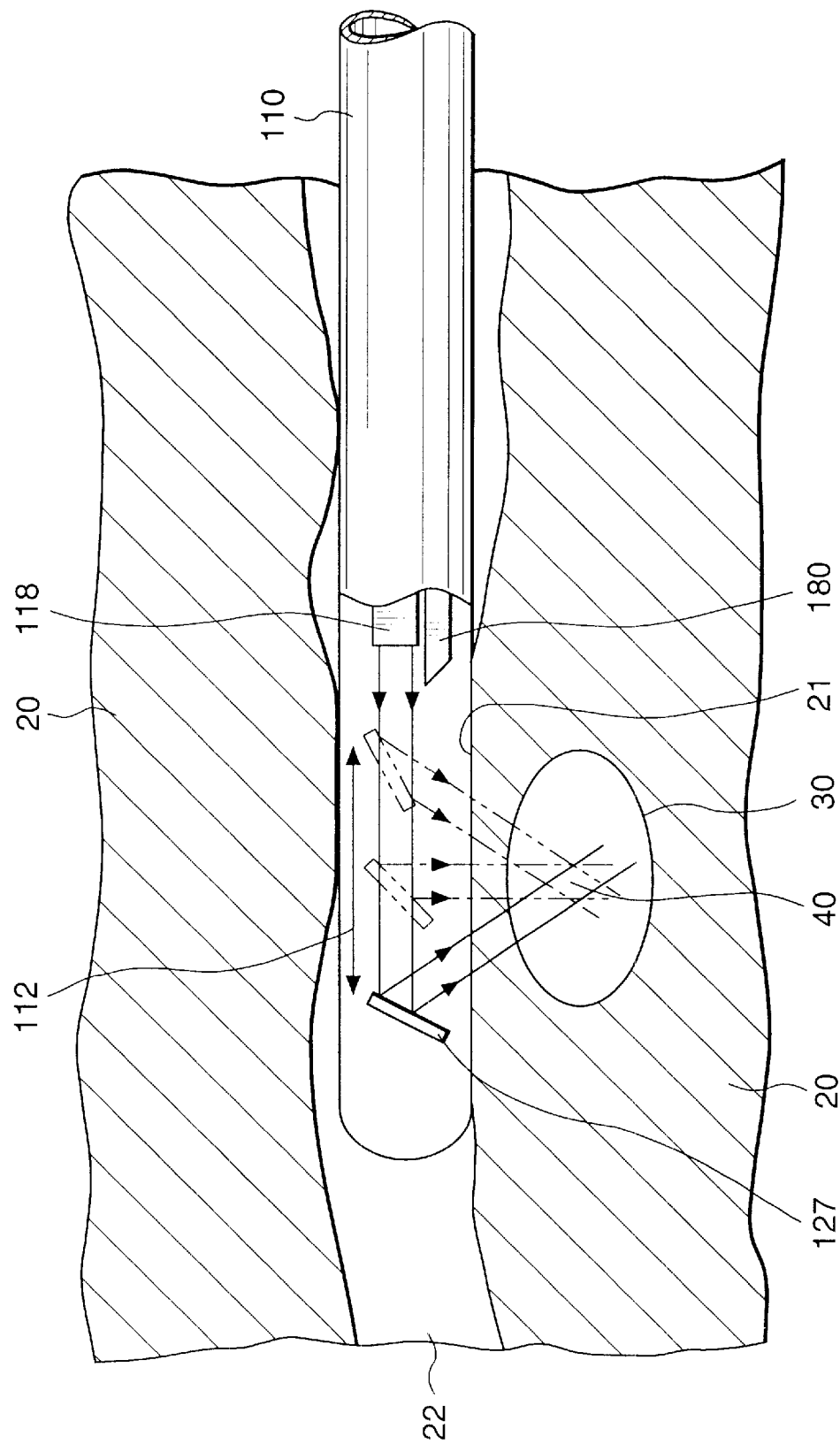
FIG. 5 is a sectional view for explaining an application of the laser beam irradiation unit 1, which shows the end portion and its vicinity inserted into a vital tissue.

FIG. 5 is a sectional view for explaining an application of the laser beam irradiation unit 1. The distal end portion of the main body front portion 110 is inserted into a body cavity 22. The housing 112 which accommodates the reflecting surface 127 is brought into tight contact with the surface layer 21 near the target portion 30 as a morbid portion, i.e., a portion to be heated.

It is desirable to directly confirm the position of the housing 112 by an endoscope 180. Note that the position of the target point 40 in the longitudinal direction of the main body front portion 110 is adjusted by moving the whole laser beam irradiation unit 1 in the longitudinal direction of the main body front portion 110.

Also, the position of the target point 40 in the circumferential direction of the main body front portion 110 can be adjusted by manually or automatically rotating the entire laser beam irradiation unit 1.

During laser beam irradiation, the reflecting surface 127 is moved back and forth in the axial direction while its angle is changed at a period of 0.1 to 10 Hz, preferably 1 to 6 Hz. Although the optical path of the laser beam is thus continuously changed, the laser beam so irradiates that all optical paths cross each other at the target point 40.

Consequently, the target point 40 and its vicinity are heated by the laser beam to reach a predetermined temperature. In this manner, only the temperature in the desired portion 30 can be raised while a temperature rise in the surface layer 21 is suppressed.

Note that the laser beam is preferably divergent light, parallel light, or convergent light. An optical system which collimates a laser beam into parallel light or convergent light can also be placed midway along the optical path of the laser beam. When the laser beam is divergent light, the emission end of the optical fiber 118 is desirably interlocked with the arm 116 to stabilize the spot diameter of the laser beam. The laser beam used is not particularly limited as long as the beam is capable of reaching a deep part in a living body. The wavelength is preferably 750 to 1,300 nm, or 1,600 to 1,800 nm.

For example, a gas laser such as an He—Ne laser, a solid laser such as an Nd—YAG laser, and a semiconductor laser such as a GaAlAs laser can be applied to the laser beam generator 2 for generating a laser beam having the above wavelength.

Also, the diameter of the insertion portion of the laser beam irradiation unit 1, i.e., the outer diameter of the main body front portion 110 is not particularly restricted, provided that the diameter allows insertion into the body cavity 22. However, the outer diameter of the main body front portion 110 is preferably about 2 to 20 mm, and more preferably, 3 to 8 mm.

Figure 6A:
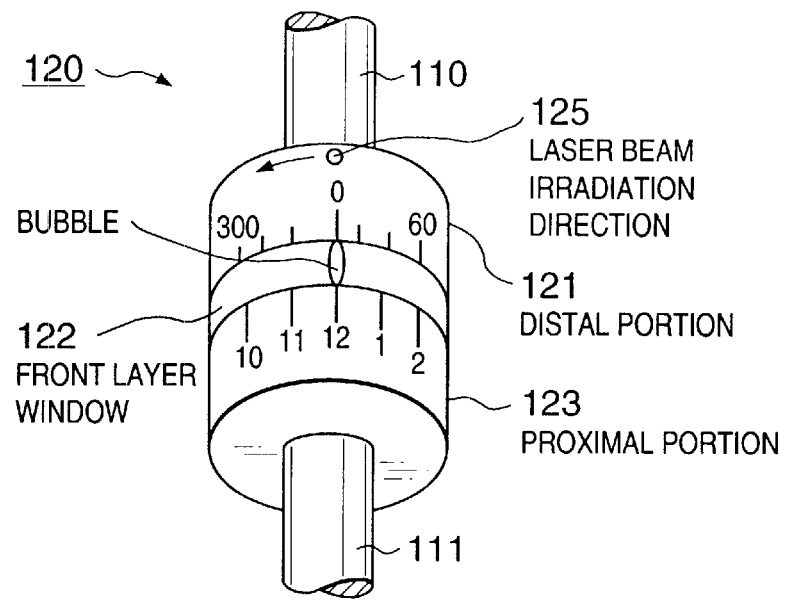
FIG. 6A is a view showing a rotational angle setting/detecting unit 120 of the first embodiment.
Figure 6B:
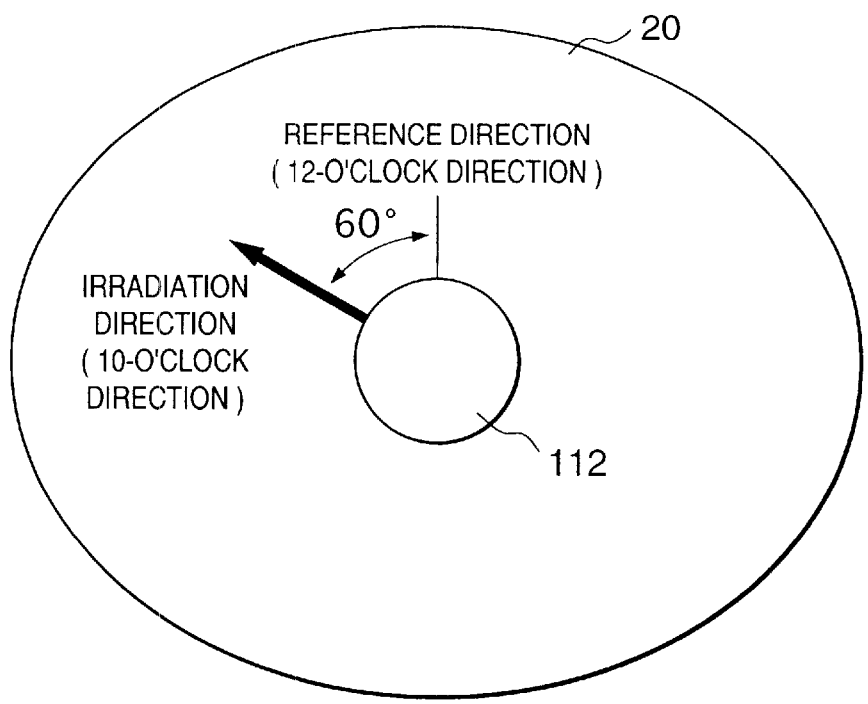
FIG. 6B is a view showing a laser beam irradiation direction matched in FIG. 6A.

FIGS. 6A and 6B are views for explaining a method of setting a direction in which a laser beam irradiates a living body by the reflecting surface 127 by using the rotational angle setting/detecting unit 120. FIG. 6A shows the rotational angle setting/detecting unit 120 of the first embodiment placed between the main body front portion 110 and the main body rear portion 111 of the laser beam irradiation unit 1.

The rotational angle setting/detecting unit 120 of the first embodiment has a rotary dial structure having distal and proximal portions 121 and 123. As shown in FIG. 1, the distal portion 121 is connected and fixed to the main body front portion 110. The proximal portion 123 is connected to the main body rear portion 111 and fixed by the driving unit 150.

The main body front portion 110 can freely rotate with respect to the main body rear portion 111 fixed to the driving unit 150.

A scale of 0° to 360° is marked on the distal portion 121, and a point indicating the irradiation direction of a laser beam, i.e., a laser beam irradiation direction 125 is formed above the position of 0°.

As shown in FIG. 6A, when this laser beam irradiation direction 125 points vertically upward, the irradiation direction of a laser beam is right above. This laser beam irradiation direction is determined by aligning the laser beam reflecting surface 127 with 0° in FIG. 6A by changing the angle in the circumferential direction of the arm 116.

The proximal portion 123 has a two-layered structure. The scale of a clock dial is marked on the rear layer. An front layer window 122 is filled with a liquid containing a bubble indicating the reference direction.

When the laser beam irradiation direction 125, i.e., 0° of the distal portion 121 is set at the position of the bubble, the laser beam irradiation direction in the circumferential direction of the laser beam irradiation unit 1 becomes opposite to the direction of gravity. Also, the laser beam irradiation direction can be defined as a 12-o'clock direction by setting 12 o'clock in the proximal portion 123 at the position of the bubble.

Note that in accordance with the shape of a vital tissue to be thermally treated, the shape of a living body into which the laser beam irradiation unit 1 is to be inserted, or the technical convenience of an operator, 12 o'clock in the proximal portion 123 can be set in a direction different from the position of the bubble to define this direction as a 12-o'clock direction. The angle information of the distal portion 121 to the proximal portion 123 can be detected electrically by the rotational angle detector 9.

An angle setting method of setting the laser beam irradiation direction in a 10-o'clock direction will be described below by taking FIG. 6B as an example.

First, as shown in FIG. 6A, the proximal portion 123 connected to the driving unit 150 is rotated to align 12 o'clock in the proximal portion 123 with the bubble position. The circumferential position of the proximal portion 123, i.e., the circumferential position of the driving unit 150 is matched with the reference position and fixed. Subsequently, 0° in the distal portion 121 is set at 12 o'clock and fixed such that the laser beam irradiation direction points in a 12-o'clock direction, thereby setting the reference direction in the 12-o'clock direction.

To set the laser beam irradiation direction at a position rotated 60° counterclockwise from the reference direction, i.e., at a 10-o'clock position in the proximal portion 123, 0° in the distal portion 121 is rotated 60° to match 10 o'clock in the proximal portion 123.

Consequently, as shown in FIG. 6B, the laser beam irradiation direction can be set in the 10-o'clock direction. In this manner, an operator can confirm the laser beam irradiation direction by visually checking the scale. If the angle information detected electrically by the rotational angle detector 9, is displayed on the display unit 7, the operator can also confirm the irradiation direction by this information.

Note that the main body front portion 110 connected to the distal portion 121 is not limited to the structure which can freely rotate with respect to the main body rear portion 111 connected to the proximal portion 123 and fixed by the driving unit 150.

For example, the distal portion 121 can also be connected to both the main body front portion 110 and the main body rear portion 111 fixed by the driving unit 150 and can freely rotate with respect to the proximal portion 123.

Figure 7:
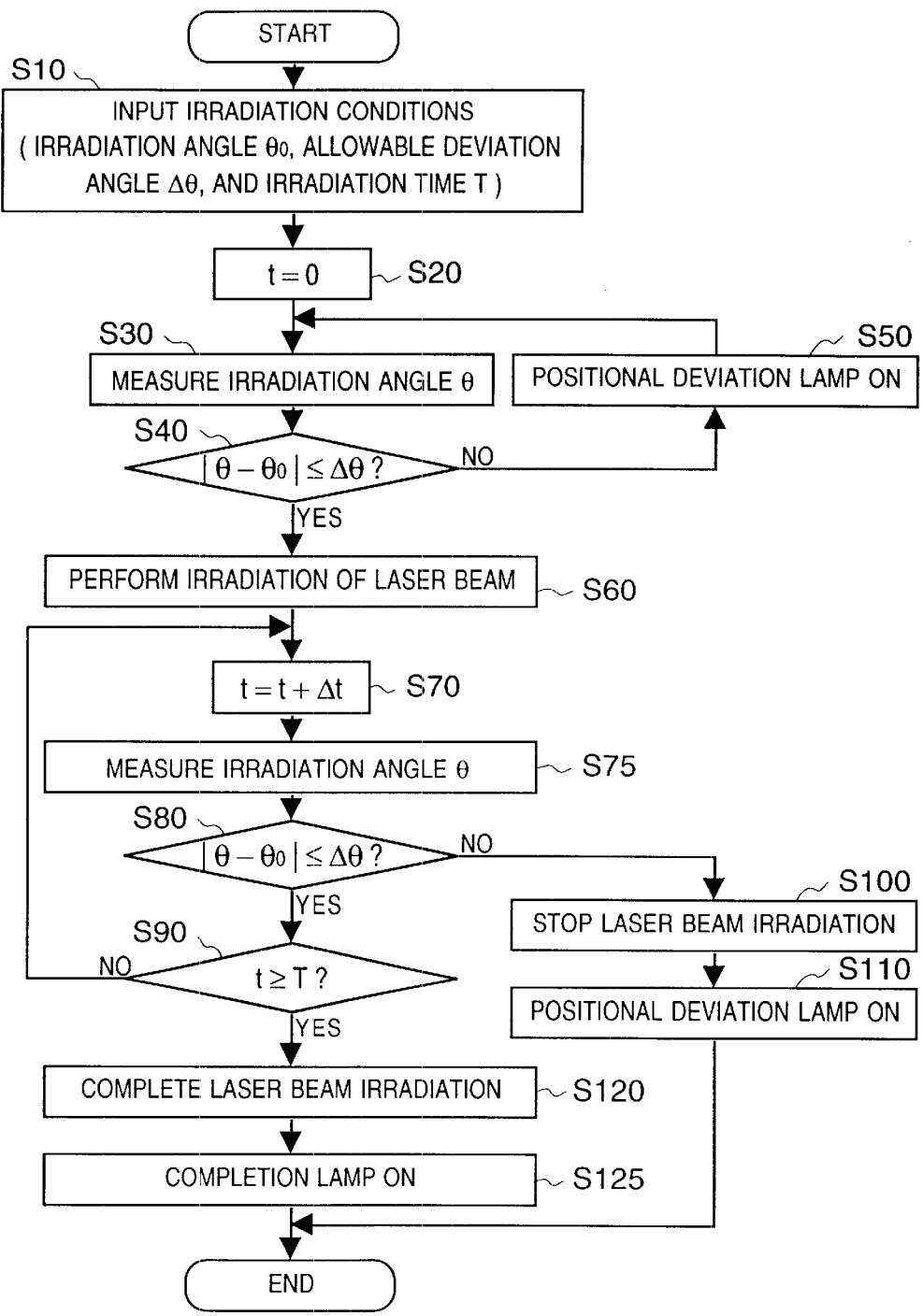
FIG. 7 is a flow chart for checking for the deviation of laser beam irradiation position in accordance with the body movement of a patient during thermal therapy in the first embodiment.

FIG. 7 is a flow chart showing a method of controlling thermal therapy using the thermal therapy apparatus 10 of this first embodiment by detecting deviation in the laser beam irradiation direction. In this first embodiment, deviation is measured using the rotational angle setting/detecting unit 120. If deviation exceeding an allowable range occurs, the therapy is immediately interrupted and restarted after the positional deviation is corrected.

In this example, to detect whether the laser irradiation direction positioned by an operator is within the allowable range and, if positional deviation occurs owing to, e.g., the movement of a patient, to detect whether the laser irradiation direction is within the allowable range, the laser irradiation direction is monitored by using the rotational angle setting/detecting unit 120 installed in the laser beam irradiation unit 1.

A program of this processing is recorded on, e.g., a ROM installed in the controller 6 shown in FIG. 1 and executed under the control of an MPU.

This flow chart will be explained below. First, an operator inputs a target laser beam irradiation direction $\theta_0$, an allowable deviation angle $\Delta\theta$, and a laser beam irradiation set time T (step S10). Note that $\theta_0$ is a counterclockwise rotational angle when the reference direction is 0°.

Subsequently, a pointer installed in the controller 6 to indicate the laser beam irradiation time is initialized to set to t=0 (step S20). The operator then inserts the laser beam irradiation unit 1 into a living body, positions the laser beam irradiation unit 1, and presses a predetermined switch on the operation unit 8 to measure a laser beam irradiation direction $\theta$ (step S30).

This laser beam irradiation direction $\theta$ is compared with the target laser beam irradiation direction $\theta_0$ (step S40). If in step 40 the difference between the laser beam irradiation direction $\theta$ and the target laser beam irradiation direction $\theta_0$ exceeds the allowable deviation angle $\Delta\theta$, the display unit 7 displays information indicating the deviation in the irradiation direction (step S50).

In this step, it is desirable to display the laser beam irradiation direction $\theta$ and the target laser beam irradiation direction $\theta_0$ by numerical values, or to display an arrow or the like on a schematic view of a vital tissue to be thermally treated, thereby permitting the operator to visually confirm the degree of the deviation in the irradiation direction.

On the other hand, if in step 40 the difference between the laser beam irradiation direction $\theta$ and the target laser beam irradiation direction $\theta_0$ does not exceed the allowable deviation angle $\Delta\theta$, the display unit 7 displays information permitting irradiation of a laser beam, so the operator presses a predetermined button on the controller 6 to perform irradiation of a laser beam (step S60).

When a time $\Delta t$ has elapsed, i.e., when the pointer installed in the controller 6 to indicate the laser beam irradiation time becomes t=t+$\Delta t$ (step S70), the laser beam irradiation direction $\theta$ is again measured (step S75) and compared with the target laser beam irradiation time $\theta 0$ (step S80). At is preferably 10 sec or less, and more preferably, 1 sec or less. If in step S80, the difference between the laser beam irradiation direction $\theta$ and the target laser beam irradiation direction $\theta_0$ does not exceed the allowable deviation angle $\Delta\theta$, whether the laser beam irradiation time has reached the laser beam irradiation set time T is checked (step S90).

If the laser beam irradiation time has reached the laser beam irradiation set time T, the controller 6 terminates the irradiation of the laser beam (step S120) The display unit 7 displays information indicating the termination of the laser beam irradiation (step S125).

If the laser beam irradiation time has not reached the laser beam irradiation set time T, the flow returns to step S70 to continue the laser beam irradiation. If instep S80 the difference between the laser beam irradiation direction $\theta$ and the target laser beam irradiation direction $\theta_0$ exceeds the allowable angle $\Delta\theta$, the controller 6 interrupts the irradiation of the laser beam (step S100), and the display unit 7 displays information indicating the interruption of the thermal therapy due to the deviation in the irradiation direction (step S110).

Figure 8:
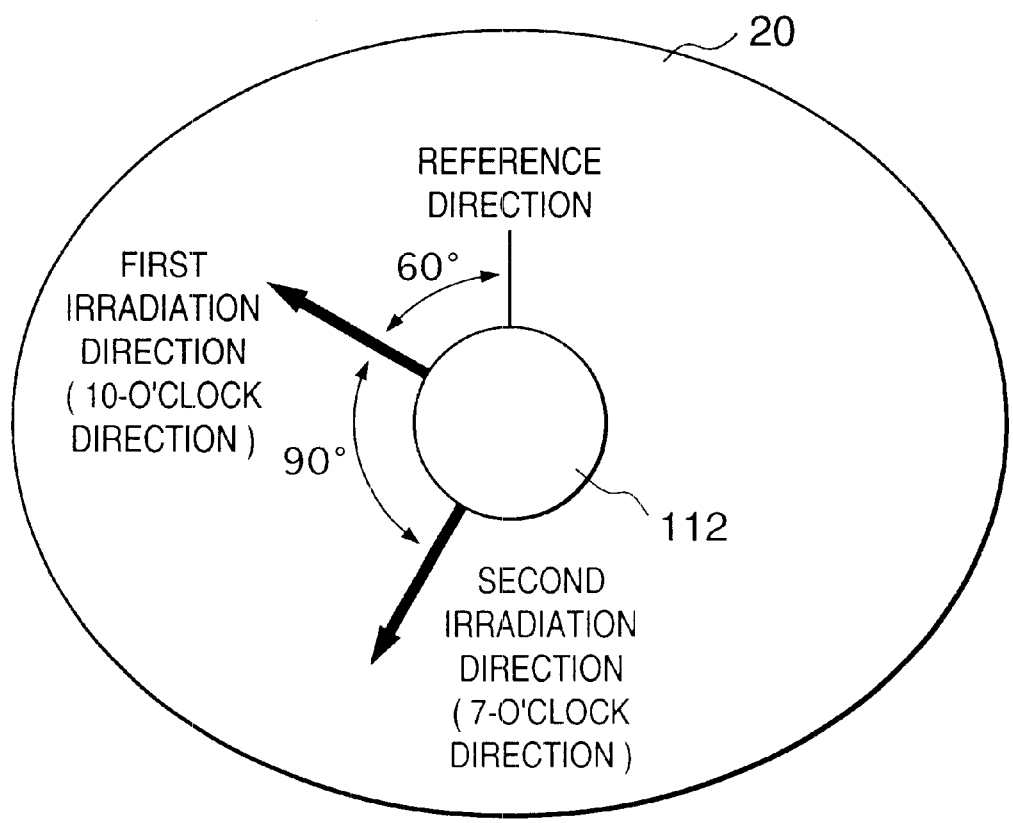
FIG. 8 is a view showing the positional relationship between irradiation direction 1 and irradiation direction 2.

A method of setting an irradiation direction when a laser beam is to irradiate in a plurality of directions will be described below by taking a case in which irradiation directions are two directions as an example. As shown in FIG. 8, a first irradiation direction is a direction of 60° (10-o'clock direction) counterclockwise from the reference direction. A second irradiation direction is a direction of 90° from the first irradiation direction, i.e., a direction of 150° (7-o'clock direction) from the reference direction.

First, a laser beam irradiation direction is set in the first irradiation direction. This method will not be explained because it is the same as described above. After a laser beam irradiates in this first irradiation direction, the laser beam irradiation direction is set in the second irradiation direction. That is, the 0° point in the distal portion 121 on which the laser beam irradiation direction 125 is marked is rotated 90° counterclockwise from the first irradiation direction and aligned with 7 o'clock in the proximal portion 123.

In this state, 150° in the distal portion 121 is positioned at the position of the bubble, i.e., the position of 12 o'clock in the proximal portion 123. By thus detecting the correspondence between a specific clock direction on the scale of the proximal portion 123 and the 0° point in the distal portion 121 or by detecting the correspondence between a specific degree on the scale of the distal portion 121 and the position of the bubble, each laser beam irradiation direction can be known. Even when irradiation directions are three or more directions, each laser beam irradiation direction can be known by a similar operation.

To prevent laser beam irradiation in the same direction due to operational error, the controller 6 can include a storage device (not shown) for storing directions in which a laser beam irradiates.

Figure 9:
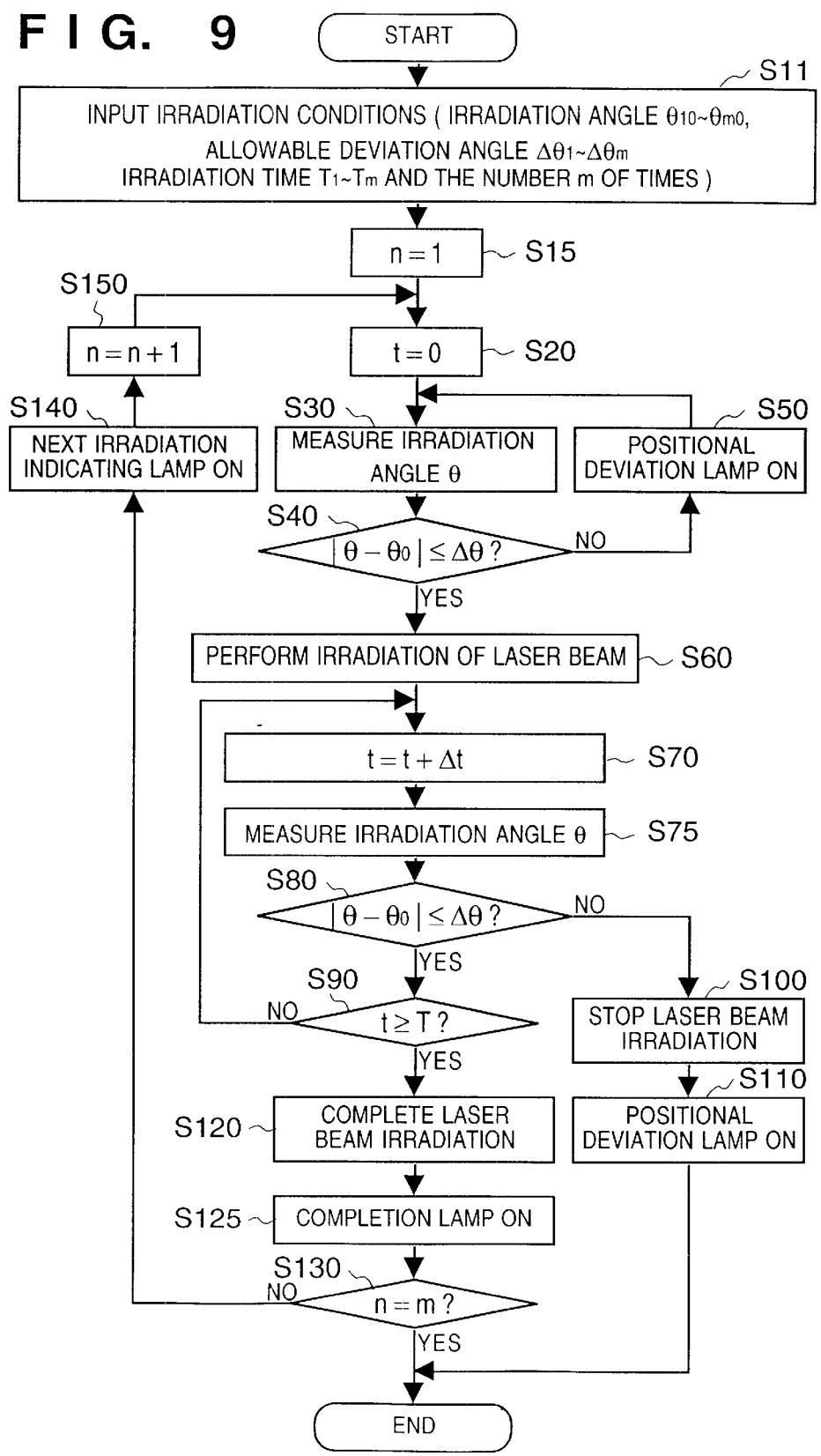
FIG. 9 is a flow chart for checking for the deviation of laser irradiation position in accordance with the body movement of a patient during thermal therapy in the first embodiment.

FIG. 9 is a flow chart showing a thermal therapy control method of detecting deviation in a laser beam irradiation direction in thermal therapy performed by making a laser beam irradiate in a plurality of directions by using the thermal therapy apparatus 10.

A description of the same points as in the flow chart shown in FIG. 7 described above will be omitted, and only differences will be explained. The flow chart in FIG. 9 shows a method which in performing therapy by making a laser beam irradiate in m directions measures deviation in each laser irradiation direction. If deviation exceeding an allowable range occurs, the therapy is immediately interrupted and restarted after the positional deviation is corrected. In this example, to detect whether each laser irradiation direction positioned by an operator is within the allowable range and, if positional deviation occurs owing to, e.g., the movement of a patient, to detect whether each laser irradiation direction is within the allowable range, each laser irradiation direction is monitored by using the rotational angle setting/detecting unit 120 installed in the laser beam irradiation unit 1.

This flow chart will be described below. First, an operator inputs the set number m of times of laser beam irradiation, target laser beam irradiation directions $\theta_{10}, \theta_{20}, \ldots, \theta_{m0}$, allowable deviation angles $\Delta\theta_1, \Delta\theta_2, \ldots, \Delta\theta m$, and laser beam irradiation set times T1, T2, . . . , Tm corresponding to the individual laser beam irradiation directions.(Step S11)

Note that $\theta_{10}, \theta_{20}, \ldots, \theta_{m0}$ are counterclockwise rotational angles when the reference direction is 0°. Subsequently, a pointer installed in the controller 6 to indicate the number of times of laser beam irradiation is initialized to set n=1 (step S15).

A procedure up to step S125 in which therapy in a first irradiation direction is completed is the same as in the flow chart shown in FIG. 7, so a detailed description thereof will be omitted.

When the therapy in the first irradiation direction is completed, whether the number n of times of laser beam irradiation has reached the set number m of times of laser beam irradiation is checked (step S130). If NO in step S130, the flow advances to step S140, and the display unit 7 displays information prompting movement to a second laser beam irradiation direction. After the direction has moved to the next laser beam irradiation direction, the operator presses a predetermined switch on the controller 6 to add 1 to the pointer installed in the controller 6 to indicate the number of times of laser beam irradiation (step S150), and the flow returns to step S20. A similar operation is repeated even when laser beam irradiation directions are three or more directions.

If the number n of times of laser beam irradiation has reached the set number m of times of laser beam irradiation, the display unit 7 displays information indicating the completion of the thermal therapy.

Figure 10:
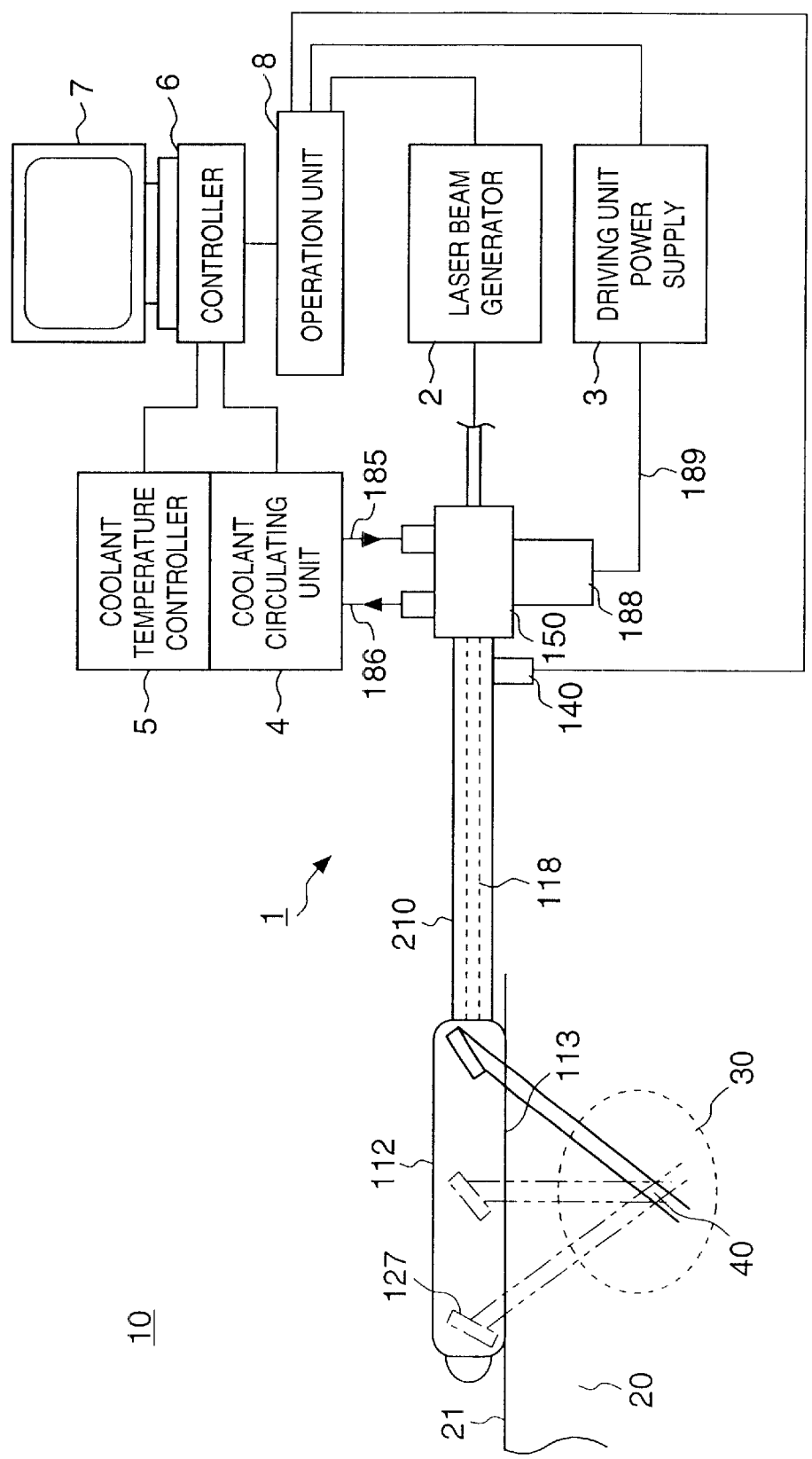
FIG. 10 is a view showing the system configuration of a thermal therapy apparatus 10 of the second embodiment.

FIG. 10 is a view showing the system configuration of a thermal therapy apparatus 10 of the second embodiment. A detailed description of this thermal therapy apparatus 10 will be omitted because a rotational angle setting/detecting unit 140 and a main body 210 of a laser beam irradiation unit 1 are the only difference from the first embodiment. This rotational angle setting/detecting unit 140 and a main body will be described below with reference to FIGS. 1A and 11B, but a description of the same points as in the first embodiment will be omitted.

Figure 11A:
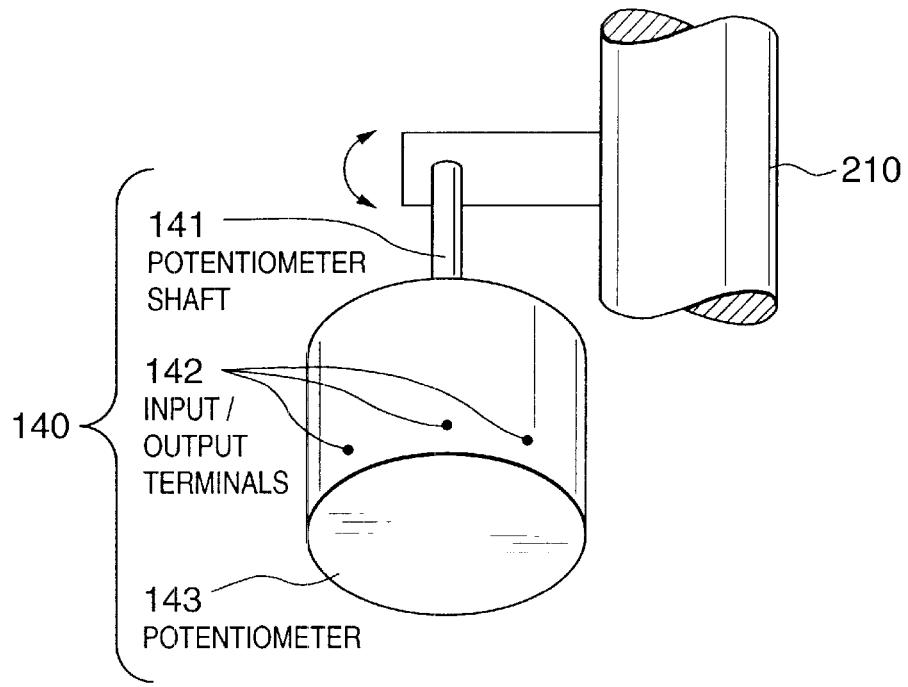
FIG. 11A is a view showing a rotational angle setting/detecting unit 140 of the second embodiment.
Figure 11B:
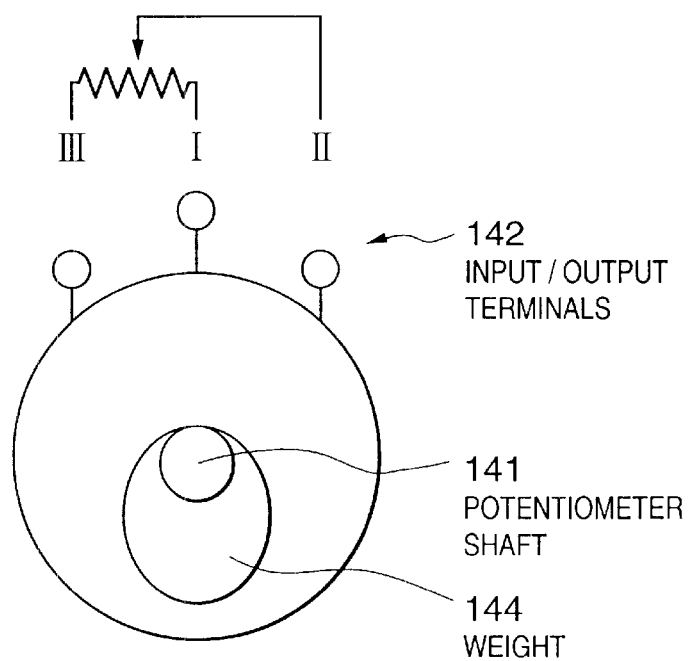
FIG. 11B is a view showing a method of detecting a rotational angle by the rotational angle setting/detecting unit 140 of the second embodiment.

FIGS. 11A and 11B are views for explaining a method of setting laser beam irradiation directions in a living body by a laser beam reflecting surface 127 by using the rotational angle setting/detecting unit 140. FIG. 11A shows the rotational angle setting/detecting unit 140 of the second embodiment installed in a main body 210 of a laser beam irradiation unit 1. This rotational angle setting/detecting unit 140 of the second embodiment is composed of a potentiometer shaft 141 and a potentiometer 143 having input/output terminals 142. The potentiometer shaft 141 is preferably detachable from the main body 210 to allow easy replacement of the main body 210.

Also, the potentiometer shaft 141 and a connecting portion of the main body 210 can have noncircular shapes such as the shapes of a key and a keyhole. Furthermore, to prevent unexpected removal, a lock mechanism can be formed in the potentiometer shaft 141 or the main body 210 to allow reliable connection.

As shown in FIG. 11B, the main body 210 of the laser beam irradiation unit 1 is rotated such that the potentiometer shaft points in the direction of gravity indicated by a weight 144, and this point is taken as a reference point. Also, the main body 210 of the laser beam irradiation unit 1 is rotated through an arbitrary angle from this reference point, and an output value from the potentiometer with respect to this arbitrary value is measured. A calibration curve indicating the relationship between the arbitrary angle and the potentiometer output value is formed and stored in a controller 6. When the main body 210 of the laser beam irradiation unit 1 is to be set at the arbitrary angle, the data of this calibration curve is used.

When thermal therapy is performed using the thermal therapy apparatus of the second embodiment, a method of detecting and correcting deviation in the laser irradiation position produced when a patient moves his or her body for some reason is the same as the flow chart shown in FIG. 7, so a detailed description thereof will be omitted.

Figure 12:
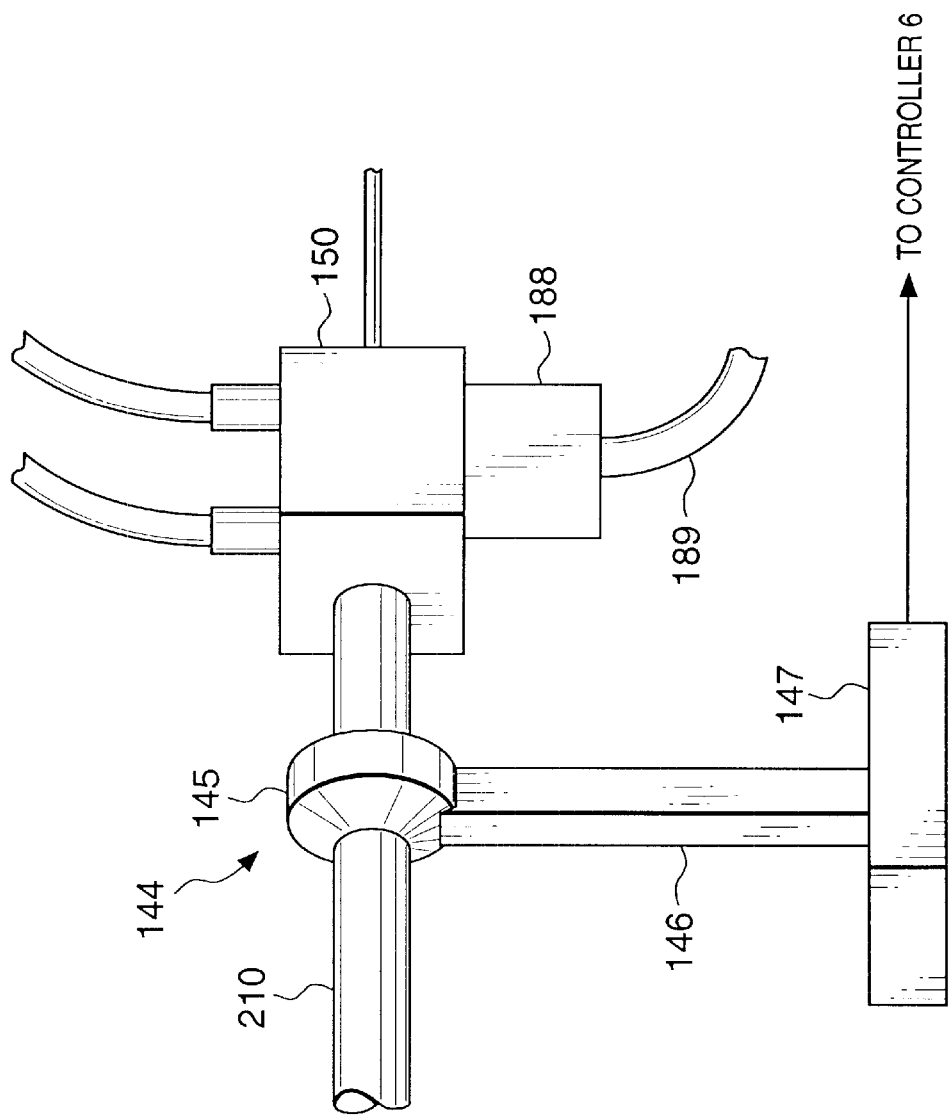
FIG. 12 is a view showing a stand member 144 as a rotational angle/position detecting means connected to a laser beam irradiation unit 1 of a thermal therapy apparatus of the third embodiment.

FIG. 12 is a view showing the construction of a stand member 144 as a rotational angle/position detecting means connected to a laser beam irradiation unit 1 of a thermal therapy apparatus 10 of the third embodiment.

The system configuration of the thermal therapy apparatus 10 of this third embodiment differs from FIG. 10 of the second embodiment described earlier only in the stand member 144 as a rotational angle setting/detecting means. Hence, a description of the system configuration and identical points will be omitted.

The stand member 144 as a rotating angle setting/detecting means as the only difference will be described below with reference to FIG. 12.

This stand member 144 as a rotational angle setting/detecting means is composed of a potentiometer member 145 having a hole in its central portion through which it can be attached to and detached from a main body 210, a columnar member 146 connected to this potentiometer member 145, and a fixed base 147. As shown in FIG. 12, the potentiometer member 145 and the main body 210 are connected by inserting the main body 210 into the central hole of the potentiometer member 145.

This potentiometer member 145 is so designed as to permit movement and rotation in the axial direction. The potentiometer member 145 incorporates a displacement sensor, such as a variable resistor or a potentiometer, which when reset at an initial position senses a moving amount and a rotating amount in the axial position from the initial position.

Information such as the position in the axial direction or the rotational angle of the main body 210 sensed by the potentiometer member 145 is transmitted as a signal to a controller 6. The fixed base 147 can be placed on a hardly moving portion of a patient or on a bed, medical table, or operating table used when thermal therapy is performed, so that the potentiometer 145 does not move.

The initial position is set by inserting the main body 210 to a desired position in a living body, e.g., to the center, back side, or front side of a vital tissue to be irradiated with a laser beam, and pressing a predetermined switch on a control unit.

In this initial position setting, a reference insertion length is preferably set by a visual check by an endoscope 180 inserted into the main body 210 or by performing image diagnosis such as MRI (Magnetic Resonance Imaging), CT (Computed Tomography) using X-rays or magnetic resonance, PET (Positron Emission Tomography), or SPECT (Single Photon Emission Computed Tomography).

The stand member 144 as a rotating angles setting/detecting means is connected to the controller 6. Similar to the rotational angle setting/detecting unit 140, the main body 210 is previously moved an arbitrary length from the reference insertion length. A calibration curve indicating the relationship between this arbitrary moving distance of the main body 210, i.e., the arbitrary moving distance of a movable part and the resistance value of a variable resistor or the output value from a potentiometer is formed, and the data is stored in the controller 6.

The main body 210 is set at the arbitrary insertion length by using this calibration curve data. A driving mechanism can also be incorporated into the potentiometer member 145 to allow insertion of the main body 210 into a living body or rotation of the main body 110 by electric power under the control of the controller 6.

When thermal therapy is performed using the thermal therapy apparatus 10 of the third embodiment, a method by which the stand member 144 as a rotational angle setting/detecting means detects and corrects deviation of a laser beam irradiation unit 1 produced when a patient moves during the therapy is the same as the flow chart in FIG. 7, so a detailed description thereof will be omitted.

Also, a method by which the potentiometer 145 detects and corrects deviation of the laser beam irradiation unit 1 can be carried out by a flow chart similar to the flow chart shown in FIG. 7 by inputting axial direction position information and an allowable deviation length, instead of the irradiation angle and the allowable deviation angle in FIG. 7.

Furthermore, by inputting all of the irradiation angle, allowable deviation angle, axial direction position, and allowable deviation length, it is possible to detect and correct deviation of the laser beam irradiation unit 1 in both the rotating direction and the longitudinal direction.

The thermal therapy apparatus of the present invention includes a device for detecting the irradiation direction of energy during thermal therapy in which energy irradiates a living body, and can thereby easily set the irradiation direction in a desired direction. The apparatus can also control the thermal therapy on the basis of the detection information.

The present invention is not limited to the above embodiments and various changes and modifications can be made within the spirit and scope of the present invention. Therefore, to apprise the public of the scope of the present invention, the following claims are made.

What is claimed is:

1. A thermal therapy apparatus for performing a medical treatment by irradiation of energy into a living body, comprising:

energy generating unit generating the energy;

a long insertion portion which can be inserted into the living body;

an emission portion formed in said insertion portion to perform lateral irradiation of the energy with respect to a longitudinal direction of said insertion potion;

direction detector detecting an irradiation direction of the energy in said insertion portion; and confirming unit notifying an operator of information about the detection by said direction detector.

2. The apparatus according to claim 1, wherein said direction detector is filled with a liquid containing a bubble which is always positioned in the opposite direction to gravity.

3. The apparatus according to claim 1, wherein said direction detector comprises at least one of a displacement sensor and an angular displacement sensor.

4. The apparatus according to claim 1, wherein the energy irradiation is irradiation of a laser beam.

5. The apparatus according to claim 1, further comprising:

moving unit for moving the position of said emission portion in the longitudinal direction of said insertion portion; and interlocking unit changing an emission angle of said emission portion in accordance with the movement in the longitudinal direction of said emission portion.

6. The apparatus according to claim 1, further comprising cooling unit cooling said emission portion and the surface and its vicinity of a living body irradiated with the energy.

7. The apparatus according to claim 1, further comprising:

position detector detecting position information in an axial direction of said insertion portion; and control unit controlling said irradiation of the energy on the basis of the position information detected by said position detector.

8. A thermal therapy apparatus for performing a medical treatment by irradiation of energy into a living body, comprising:

energy generating unit generating the energy;

a long insertion portion which can be inserted into a living body;

an emission portion formed in said insertion portion to perform lateral irradiation of the energy with respect to a longitudinal direction of said insertion potion;

direction detector detecting an irradiation direction of the energy in said insertion portion; and controller controlling said irradiation of the energy on the basis of information about the detection by said direction detector.

9. The apparatus according to claim 8, wherein said direction detector is filled with a liquid containing a bubble which is always positioned in the opposite direction to gravity.

10. The apparatus according to claim 8, wherein said direction detector comprises at least one of a displacement sensor and an angular displacement sensor.

11. The apparatus according to claim 8, wherein the energy irradiation is irradiation of a laser beam.

12. The apparatus according to claim 8, further comprising:

moving unit moving the position of said emission portion in the longitudinal direction of said insertion portion; and interlocking unit changing an emission angle of said emission portion in accordance with the movement in the longitudinal direction of said emission portion.

13. The apparatus according to claim 8, further comprising cooling unit cooling said emission portion and the surface and its vicinity of a living body irradiated with the energy.

14. The apparatus according to claim 8, further comprising:

position detector detecting position information in an axial direction of said insertion portion; and control unit for controlling said irradiation of the energy on the basis of the position information detected by said position detector.

* * * * *

UNITED STATES PATENT AND TRADEMARK OFFICE
CERTIFICATE OF CORRECTION

PATENT NO. : 6,468,267 B1
DATED : October 22, 2002
INVENTOR(S) : Shigeki Ariura

It is certified that error appears in the above-identified patent and that said Letters Patent is hereby corrected as shown below:

Column 8,
Line 38, delete "At" and insert -- $\Delta t$ --.
Line 52, delete "instep" and insert -- in step --.

Column 9,
Lines 36, 49 and 65, delete "m" and insert -- $\underline{m}$ --.
Line 64, delete "n" and insert -- $\underline{n}$ --.

Column 10,
Line 10, delete "n" and insert -- $\underline{n}$ --.
Line 11, delete "m" and insert -- $\underline{m}$ --.

Signed and Sealed this

First Day of July, 2003

JAMES E. ROGAN
*Director of the United States Patent and Trademark Office*